(12) United States Patent
Beimier et al.

(10) Patent No.: US 7,014,362 B2
(45) Date of Patent: Mar. 21, 2006

(54) DEVICE FOR DETERMINING RELATIVE POSITIONS OF AN X-RAY SOURCE AND AN IMAGE RECEIVER

(75) Inventors: Franz Beimier, Weiden (DE); Franz Dirauf, Ebensfeld (DE); Karlheinz Kaul, Neunkirchen (DE); Donal Medlar, Weisendorf (DE); Claus-Günter Schliermann, Kamnath (DE); Martin Vierbücher, Ebern (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/935,325

(22) Filed: Sep. 7, 2004

(65) Prior Publication Data

US 2005/0058256 A1    Mar. 17, 2005

(30) Foreign Application Priority Data

Sep. 9, 2003    (DE) .............................. 103 41 541

(51) Int. Cl.
    *A61B 6/08* (2006.01)
(52) U.S. Cl. .................. 378/206; 378/19; 378/162
(58) Field of Classification Search ............... 378/204, 378/205, 206, 207, 19, 162
    See application file for complete search history.

(56) References Cited

U.S. PATENT DOCUMENTS

| | | | |
|---|---|---|---|
| 6,447,164 B1 * | 9/2002 | Polkus | 378/206 |
| 6,731,718 B1 | 5/2004 | Ogura et al. | 378/63 |

FOREIGN PATENT DOCUMENTS

| | | |
|---|---|---|
| DE | 196 11 705 A1 | 10/1997 |
| DE | 196 29 109 A1 | 1/1998 |
| DE | 101 18 183 A1 | 11/2002 |

* cited by examiner

*Primary Examiner*—Edward J. Glick
*Assistant Examiner*—Courtney Thomas
(74) *Attorney, Agent, or Firm*—Brinks Hofer Gilson & Lione

(57) ABSTRACT

A device for detecting an orientation and spacing of an X-ray source relative to an X-ray receiver comprises a projector which is disposed at a predetermined orientation and a predetermined spacing relative to the X-ray source, and is configured to project a predetermined pattern of electromagnetic waves in a direction of the X-ray receiver. A detector is configured to detect the predetermined pattern projected by the projector. A positioning detection device, connected to the detector and configured to receive an output signal from the detector, generates a positioning signal as a function the output signal. The positioning signal comprises information about the orientation and spacing of the X-ray source relative to the X-ray receiver.

21 Claims, 2 Drawing Sheets

DEVICE FOR DETERMINING RELATIVE POSITIONS OF AN X-RAY SOURCE AND AN IMAGE RECEIVER

FIELD OF THE INVENTION

The invention relates to, generally, to X-ray systems, and more particularly to a device for determining relative positions of an X-ray source and an image receiver of an X-ray system.

BACKGROUND OF THE INVENTION

X-ray systems typically serve to pass X-radiation through bodies in various directions and with various orientations. An X-ray source generates an X-ray beam, which passes through a body to be examined and is then received by an X-ray receiver. Various orientations in three dimensions are achieved by providing that the X-ray source can be positioned and oriented variably in terms of three dimensions. So that the X-ray beam can be picked up, the X-ray receiver is positioned in a predetermined position relative to the X-ray source.

An image section, image geometry, and a quality of an X-ray image can be affected by the relative position of the X-ray source and the X-ray receiver. Incorrect or imprecise positioning can cause problems that may necessitate retaking unsuccessful radiographs, which involves considerable effort on the part of medical personnel as well as additional radiation exposure to the body of a patient, for instance, who is to be examined.

Substantially precise relative positioning of the X-ray source and X-ray receiver can be attained using a light collimator, for instance. The light collimator projects an optical image, such as crosshairs, from the X-ray source and this image can be aligned with the X-ray receiver by a machine operator or user. The manual alignment can involve considerable operator effort, and may only conditionally enable exact setting of the direction, spacing and orientation. The spacing and orientation cannot be adequately exactly perceived by the machine operator on the basis of an optical projection. Light collimators are therefore primarily employed for aligning the X-ray source with the body region to be examined.

For substantially exact detection of the relative positioning, angle encoders and travel pickups are usually utilized in the mechanism of an X-ray system. For example, the X-ray source can be mounted horizontally displaceable, vertically adjustable, and rotatable about both a vertical and a horizontal axis on a ceiling-mounted tripod. Such a tripod can enable a completely flexible three-dimensional mobility of the X-ray source. To detect the three-dimensional position and orientation at a given time, travel pickups are mounted on the X-ray system mechanism for the horizontal displacement and vertical adjustment, and angle encoders are mounted on the axes for the horizontal and vertical rotation.

Via the travel pickups, the three-dimensional orientation and position of the X-ray source are accordingly fundamentally detectable, as are those of the X-ray receiver. However, a plurality of pickups is needed, which increases a vulnerability or susceptibility to error because of compounding measurement tolerances. Moreover, the measurement is subject to errors due to a heavy weight, for instance of an X-ray source, an elasticity, for instance of a ceiling-mounted tripod, and because typically components deform elastically under load. The component deformation, however, cannot be detected by the travel pickups and angle encoders.

From German Patent Disclosure DE 196 11 705, it is known, instead of indirect detection by travel pickups and angle encoders, to provide for direct detection of the orientation and position, that is, a detection of the actual state. As such, measuring mechanisms that enable detecting the three-dimensional position, or position in space, are mounted on the X-ray source and on the X-ray receiver. The relative three-dimensional position can be ascertained or determined using t space coordinates. The indirect nature of determining the relative position by first ascertaining the current three-dimensional position can increase the vulnerability to error. Moreover, the measuring mechanisms for ascertaining a given position in space are complicated because, to ascertain the respective orientation, the space coordinates of all three points for a device must be ascertained.

OBJECT AND SUMMARY

The present invention is defined by the appended claims. This description summarizes some aspects of the present embodiments and should not be used to limit the claims.

An object is to disclose a substantially reliable, and inexpensively feasible, device for ascertaining the relative position of an X-ray source and an X-ray receiver.

One concept is a device for detecting the orientation and spacing of an X-ray source relative to an X-ray receiver, which has a projector which is disposed at a predetermined orientation and a predetermined spacing relative to the X-ray source and is configured to project a predetermined pattern of electromagnetic waves. The device has a detector which is configured to detect the wave pattern projected by the projector in the direction of an X-ray receiver. The device has a positioning detection unit, which is connected to the detector and configured to receive an output signal from the detector and, as a function of a reception of the output signal, generate a positioning signal which includes information about the orientation and spacing of the X-ray source relative to the X-ray receiver.

The properties of the projected wave pattern, such as size, length and distortion, enable the direct ascertainment of the relative position of the X-ray source to a corresponding projection face. In order to be able to ascertain the relative position of the X-ray source and the X-ray receiver, it therefore suffices to detect the wave pattern projected onto the projection face. The X-ray receiver can serve as the projection face, or another face of known orientation and known spacing from the X-ray receiver can be used.

The device has a simple construction, because instead of two sensors each operating separately for ascertaining positions in space, only one detector is needed for ascertaining the relative position. Furthermore, the detector is based on a simple measurement principle, which can be realized using geometrical structures and basic methods of linear algebra. One may dispense with additional position determining signals, such as infrared or radio frequency signals, and as a result the exposure to additional interference signals can be kept slight. Instead of the named signal types, the projection of the wave pattern may be done for instance using visible light or X-radiation.

In an advantageous feature, the projector is an optical projector, and the detector is an optical detector. The use of optical components that employ visible light can substantially simplify the manipulation of the device by machine operators. On the one hand, visible light causes no unnecessary radiation exposure, and on the other hand, visible light makes the device easier to manipulate whenever automated manipulations are not provided.

In a further advantageous feature, the optical detector is disposed at a predetermined orientation and a predetermined spacing relative to the X-ray source. In this feature, the device detects indirectly the pattern projected by visible light, since the pattern is projected in the direction of the X-ray receiver and is detected once reflected in the opposite direction. For example, the optical detector may be configured as a camera by which the reflected pattern is scanned. The disposition of both the projector and the detector at the X-ray source makes the device simpler, in the sense that the X-ray receiver can be left unaltered. Structural and installation provisions may be required solely at the X-ray source.

In a further advantageous feature, a diaphragm may be disposed at the X-ray source, and the X-ray source in conjunction with the diaphragm may form the projector. The diaphragm may be manufactured specifically for a desired projection of the pattern, or may be a multileaf diaphragm suitably designed and provided with the X-ray source. In that case, the structural effort and expense for realizing the projector may be substantially avoided. At least one additional diaphragm, inserted into the X-ray beam path, for instance, in addition to the multileaf diaphragm that is typically present, or instead of it, may be used. As such, the X-ray source need not be provided with additional electronic components, such as an additional optical emitter.

In a further advantageous feature, the X-ray receiver may comprise the detector. As a result, all the structural provisions required for the X-ray receiver are dispensed with. Instead, the already existing construction inside the X-ray system can be used unaltered.

In a further advantageous feature, the detector is configured as an X-ray detector and can be disposed at a predetermined orientation and at a predetermined spacing or position in relation to the X-ray receiver. As such, regardless of the existing X-ray receiver, one may use a suitable detector. For instance, if the X-ray receiver on the basis of a film-screen system is used, a digital detector can be employed so as to have an electronic detector output signal available. Moreover, a separately provided detector can be used independently of any later replacement of the X-ray receiver, without requiring recalibration of the detector signals.

In a further advantageous feature, the projector is configured to project a geometric pattern. Such a pattern can help ascertain the spacing and orientation via basically simple methods of linear algebra. For instance, it may suffice to detect spacing, lengths, or distortions of the pattern.

Illustrative and exemplary embodiments of the invention are described in further detail below with reference to and in conjunction with the figures.

DETAILED DESCRIPTION OF DRAWINGS

Figure 1:
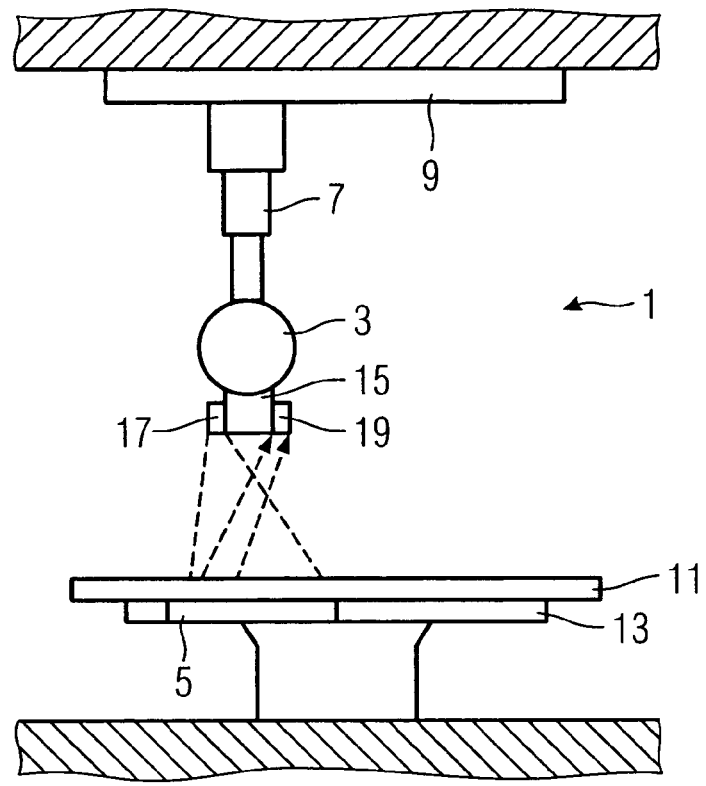
FIG. 1 illustrates schematically an X-ray system with a device for detecting a relative position of an X-ray source and an X-ray receiver.

In FIG. 1, an X-ray system 1 with a device for detecting the relative position of an X-ray source 3 and an X-ray receiver 5 is schematically shown. The X-ray source 3 is secured and vertically adjustable on a ceiling-mounted telescoping arm 7. The ceiling-mounted telescoping arm 7 is guided and horizontally displaceable in a ceiling rail 9. In addition to the vertical and horizontal movability, the X-ray source 3 can be rotated about a horizontal and a vertical axis, which is not shown in further detail in the drawing.

A collimator or diaphragm 15 through which the X-radiation is emitted is disposed at or affixed to the X-ray source 3. The diaphragm 15 is configured such that the X-radiation extends in the direction of a patient examination or treatment tabletop 11, the radiation having a circumference of a desired image section.

An X-ray receiver 5 is disposed below the patient examination tabletop 11. The X-ray receiver 5 is located in an image receiver rail 13, in which it can be displaced horizontally. The X-ray receiver 5 can furthermore be hinged upward about a horizontal axis, which is not shown in the drawing.

A patient, also not shown, to be examined is placed on the tabletop 11 in such a way that the X-radiation passes from the X-ray source 3 through a patient body region to be examined. Then, the X-radiation passes through the X-ray-permeable tabletop 11 and is picked up or collected by the X-ray receiver 5. For a substantially precise image section and for a desirable quality of the image taken, the orientation or alignment of the X-ray source 3 with the X-ray receiver 5 and its spacing from it are of significance.

An optical projector 17 is mounted on the diaphragm 15. The orientation and spacing of the optical projector 17 relative to the X-ray source 3 are fixedly predetermined by the mounting on the diaphragm 15. The optical projector 17 executes the same rotational and displacement motions as the X-ray source 3. The projector 17 is oriented such that its projection beam strikes approximately the same area as the X-radiation of the X-ray source 3. That is, the projection beam should extend essentially in the direction of the X-ray receiver 5.

Also mounted on the diaphragm 15 is an optical detector 19. The optical detector 19 is configured to detect visible light at the wavelengths that are projected by the optical projector 17. The optical projector 19 is likewise oriented approximately in the direction of the X-ray beam. As such, the optical detector can detect visible light that the optical projector 17 emits in this direction and that is reflected from the substantially opposite direction, for instance by the surface of the X-ray receiver 5 or of the tabletop 11.

With the prerequisite that the X-ray source 3 is oriented approximately at the X-ray receiver 5, the image projected by the optical projector 17 strikes the tabletop 11, substantially above the X-ray receiver 5. The projection created there can be detected by the optical detector 19. Because the optical projector 17 and the optical detector 19 are offset from one another, there is a different, independent beam path in each case for the projection and for the detection. If a known geometric pattern is projected, then depending on the orientation of the optical projector 17, distortions occur in the projection onto the patient tabletop 11, and because of the different beam path these distortions are detected by the optical detector 19. If a square pattern, for instance, is projected, then if the projection face is not vertically oriented, distortions occur, which can be ascertained from the fact that the projection of the square may no longer have any right angles. Such distortions in the geometric pattern that is projected and detected again can be used to ascertain the orientation of the optical projector 17 relative to the tabletop 11. Because of the fixed mounting of the optical projector 17 at the X-ray source 3, a direct conclusion about the orientation of the optical projector 17 can therefore be drawn.

Depending on the spacing of the optical projector 17 from the patient table 11, alterations furthermore occur in typical spacing and lengths of the projected geometric pattern, and these can likewise be detected by the optical detector 19. From these alterations, a substantially direct conclusion can be drawn about the spacing of the X-ray source 3.

Figure 2:
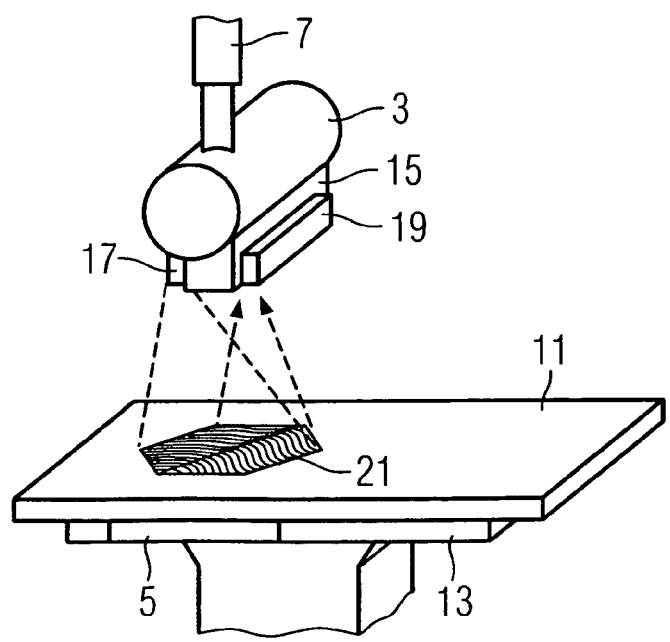
FIG. 2 is a perspective view of the device of FIG. 1, along with a projected geometric pattern.

In FIG. 2, a perspective view of part of the projected geometric figure is shown. The X-ray source 3, mounted on the ceiling-mounted telescoping arm 7, emits X-radiation in the direction of the tabletop 11, via the diaphragm 15. The X-ray receiver 5 is disposed in the image receiver rail 13, below the X-radiation-permeable tabletop 11.

Via the optical projector 17, a geometric pattern 21 is projected onto the tabletop 11. The beam path of the optical projector 17 is indicated by dashed lines. The projection of the pattern 21 on the table is detected by the optical detector 19. The detection angle is likewise indicated by dashed lines.

Figure 3:
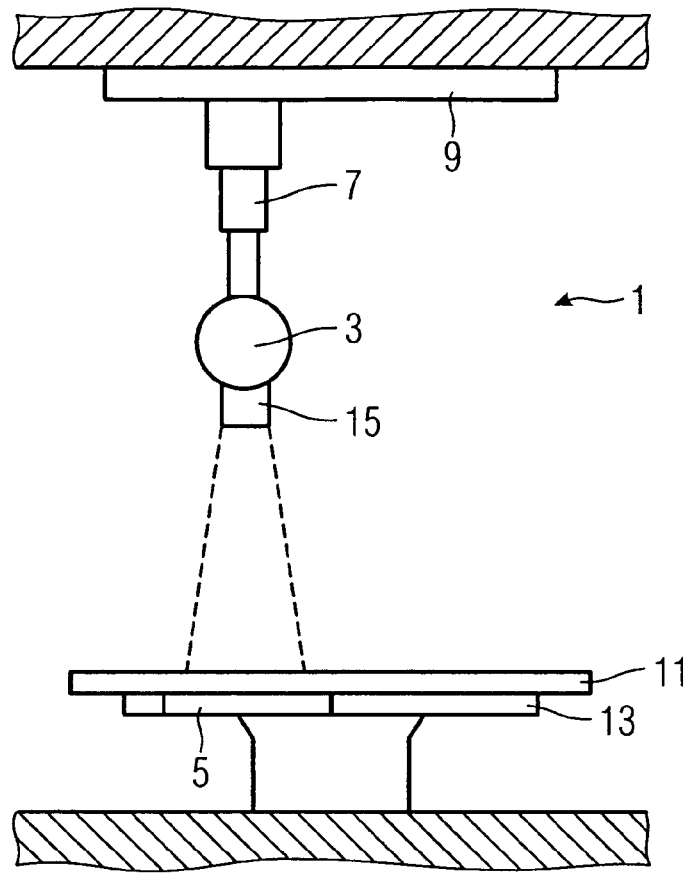
FIG. 3 illustrates schematically the X-ray system with an X-ray source and a multileaf diaphragm configured as a projector.

FIG. 3 shows an X-ray system 1 in a side view, and illustrates an X-ray source 3, which is vertically adjustable via a ceiling-mounted telescoping arm 7. The ceiling-mounted telescoping arm 7 is suspended while being horizontally displaceable from a ceiling rail 9. Via a diaphragm 15, the X-ray source 3 emits X-radiation in the direction of the tabletop 11. The path of the X-radiation is indicated by dashed lines.

The tabletop 11 is permeable to X-radiation, and an X-ray receiver 5, which is horizontally displaceable in an image receiver rail 13, is disposed beneath it. Other possibilities for displacement or rotation of the X-ray receiver 5 and of the X-ray source 3 are contemplated but are not shown in the drawing for the sake of simplicity.

A patient to be examined, likewise not shown in the drawing, is positioned on the tabletop 11 such that the X-radiation passes through the region of his body that is to be examined. The X-ray source 3 and the X-ray receiver 5 must be oriented relative to one another such that the X-ray beam, after passing through the body region to be examined, strikes the X-ray receiver 5.

To enable ascertaining the spacing and the orientation of the X-ray source 3 relative to the X-ray receiver 5, the X-ray source 3 projects a known X-radiation pattern, predetermined by the diaphragm 15, onto the X-ray receiver 5. The X-ray receiver 5 detects a projection of this pattern whose distortions allow conclusions to be drawn about the orientation and whose dimensions allow conclusions to be drawn about the spacing between the X-ray source 3 and the X-ray receiver 5. The projected pattern can be predetermined by the diaphragm 15 that is used in the X-ray system 1. In a further embodiment, the pattern can be generated by a diaphragm 15 provided separately for the purpose, which is thrust into the beam path in addition to or instead of the diaphragm 15.

Figure 4:
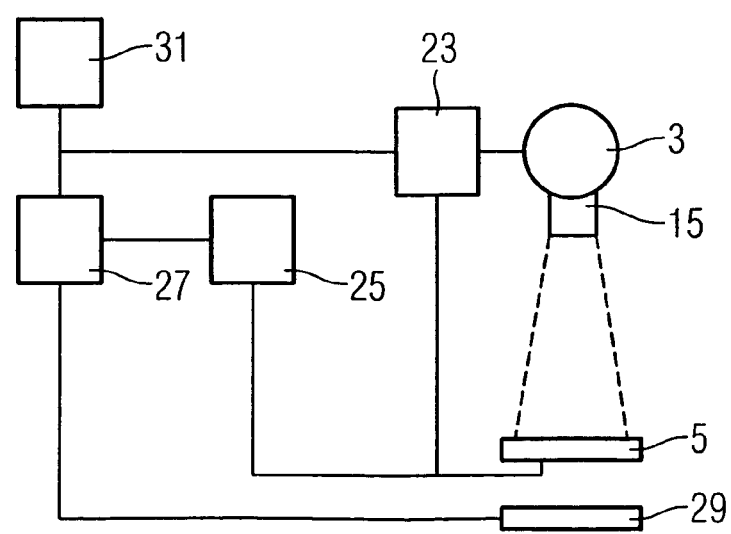
FIG. 4 is a schematic illustration of the device with corresponding components for detecting the relative position of an X-ray source and an image receiver.

In FIG. 4, the device and its components configured for ascertaining the orientation and spacing between the X-ray source 3 and the X-ray receiver 5 are shown schematically. The device functions on the basis of an X-ray projection that is generated using the standard diaphragm 15 of the X-ray system. The beam path of the X-radiation is indicated by dashed lines in the drawing. The beam strikes the X-ray receiver 5, and after passing through it, it strikes the X-ray detector 29. Both generating X-radiation and the position of the X-ray receiver 5 and of the X-ray source 3 are controlled by a control device 23.

An output signal of the X-ray receiver 5 is received by an image processor 25. This image processor 25, as a function of the output signal, which in this sense can be conceived of as raw image data, generates two-dimensional image data which represent the X-ray projection at the X-ray receiver 5. The two-dimensional image data are output as an output signal and received by the positioning detection device 27. From the two-dimensional image data, the positioning detection device 27 generates a signal which includes information about the orientation and spacing between the X-ray source 3 and the X-ray receiver 5.

For ascertaining or confirming this information, the positioning detection device 27 compares a known pattern, which is projected by the use of the diaphragm 15, with its two-dimensional projection collected by the X-ray receiver 5. Detected distortions in the projection provide information about the orientation, while typical dimensions of the projection provide information about the spacing. The known projected pattern is stored in memory for this purpose in the positioning detection device 27, or is accessible by the positioning detection device in a memory, not shown.

In the embodiment shown, one additional X-ray detector (not shown) may be provided by which further projection image data are generated. The X-ray detector may be disposed such that a known orientation and a known spacing relative to the X-ray receiver 5 are assumed, for instance being placed on the tabletop 11 or inserted into the image receiver rail 13 instead of the X-ray receiver 5. The use of the X-ray detector 29 to be provided separately enables the use of the digital device even for instance in X-ray systems that operate on the basis of an analog film-screen system, instead of a digital X-ray receiver 5.

The positioning detection device 27 generates an output signal that is displayed on a display device 31. From this display, a machine operator can tell whether the orientation and spacing between the X-ray source 3 and the X-ray receiver 5 are correct, and can make manual corrections if needed. Further, an output signal is output to the control device 23 and can be used to correct the orientation and spacing automatically. For instance, the X-ray source 3 may be configured to track automatically in reaction to a manual displacement of the X-ray receiver 5. Moreover, if the relative position is not correct, the control device 23 can prevent radiographs from being taken, so as to avoid radiographs of inadequate quality and hence an unnecessary radiation exposure to the patient.

The device for detecting the relative position can furthermore be used even with conventional film-screen systems and storage screens, because then the geometric pattern is projected onto them by X-radiation, and the projection on the film or screen is detected by using a scanner.

The device for ascertaining the relative position can also be used, in making radiographs, for simultaneously ascertaining the relative position without maintaining a correct relative position between the X-ray source 3 and the X-ray receiver 5. Instead, distortions or geometric deviations from the radiograph are compensated for if needed afterward on the basis of the information that was obtained during the generation of the radiograph as a result of the ascertainment of the relative position of the X-ray source 3 to the X-ray receiver 5.

This possibility of using the device for ascertaining the relative position exists solely whenever the device operates on the basis of an X-ray beam projection. In contrast, the ascertainment of the relative position cannot be done on the basis of an optical projection if a patient is in the projection path, for instance, and is an obstacle to the projection.

In the embodiment described above, the device for ascertaining the relative position between the X-ray source 3 and the X-ray receiver 5 has been described such that a pattern 21 is projected from the X-ray source 3 in the direction of the X-ray receiver 5. However, the mode of operation described can also be realized if the pattern 21 is conversely projected from the X-ray receiver 5 in the direction of the X-ray source 3, or in other words if the projector is disposed not on the X-ray source 3 but on the X-ray receiver 5.

What is claimed is:

1. A device for detecting an orientation and/or spacing of an X-ray source relative to an X-ray receiver, the device comprising:
   a projector disposed at a predetermined orientation and/or a predetermined spacing relative to the X-ray source, the projector operable to project a predetermined pattern of electromagnetic waves in a direction of the X-ray receiver;
   a detector operable to detect the predetermined pattern projected by the projector; and
   a positioning detection device connected with the detector and operable to receive an output signal from the detector, the positioning detection device operable to generate a positioning signal as a function the output signal,
   wherein the positioning signal comprises information about the orientation and/or spacing of the X-ray source relative to the X-ray receiver.

2. The device of claim 1, wherein the projector comprises an optical projector and the detector comprises an optical detector.

3. The device of claim 2, wherein the detector is disposed at a predetermined orientation and a predetermined spacing in relation to the X-ray source.

4. The device of claim 1, further comprising a diaphragm affixed to the X-ray source,
   wherein the projector comprises the X-ray source in conjunction with the diaphragm.

5. The device of claim 4, wherein the detector comprises the X-ray receiver.

6. The device of claim 4, wherein the detector comprises an X-ray detector and is disposed at a predetermined orientation and at a predetermined spacing in relation to the X-ray receiver.

7. The device of claim 1, wherein the projector is configured to project a geometric pattern.

8. The device of claim 2, wherein the projector is configured to project a geometric pattern.

9. The device of claim 3, wherein the projector is configured to project a geometric pattern.

10. The device of claim 4, wherein the projector is configured to project a geometric pattern.

11. The device of claim 5, wherein the projector is configured to project a geometric pattern.

12. The device of claim 6, wherein the projector is configured to project a geometric pattern.

13. An X-ray system having a device for detecting an orientation and spacing of an X-ray source relative to an X-ray receiver of the x-ray system, the device comprising:
    a projector disposed at a predetermined orientation and a predetermined spacing relative to the X-ray source, and configured to project a predetermined pattern of electromagnetic waves;
    a detector configured to detect the predetermined pattern projected by the projector in the direction of an X-ray receiver; and
    a positioning detection device connected to the detector, configured to receive an output signal from the detector, and operable to generate a positioning signal as a function the output signal,
    wherein the positioning signal comprises information about the orientation and spacing of the X-ray source relative to the X-ray receiver.

14. The X-ray system of claim 13, wherein the projector comprises an optical projector, and the detector comprises an optical detector.

15. The X-ray system of claim 13, wherein the detector is disposed at a predetermined orientation and a predetermined spacing in relation to the X-ray source.

16. The X-ray system of claim 13, further comprising a diaphragm affixed to the X-ray source,
    wherein the X-ray source in conjunction with the diaphragm is configured as the projector.

17. The X-ray system of claim 13, wherein the X-ray receiver is configured as the detector.

18. The X-ray system of claim 17, wherein the detector is an X-ray detector and is disposed at a predetermined orientation and at a predetermined spacing in relation to the X-ray receiver.

19. The X-ray system of claim 13, wherein the projector is configured to project a geometric pattern.

20. The X-ray system of claim 14, wherein the projector is configured to project a geometric pattern.

21. The X-ray system of claim 16, wherein the projector is configured to project a geometric pattern.

* * * * *

UNITED STATES PATENT AND TRADEMARK OFFICE
CERTIFICATE OF CORRECTION

PATENT NO.           : 7,014,362 B2                                         Page 1 of 1
APPLICATION NO.  : 10/935325
DATED                  : March 21, 2006
INVENTOR(S)         : Franz Beimler et al.

It is certified that error appears in the above-identified patent and that said Letters Patent is hereby corrected as shown below:

On the Title Page

Item (12), replace "Beimier" with --Beimler--.

Item (75), replace "Beimier" with --Beimler--.

Signed and Sealed this

Seventeenth Day of November, 2009

David J. Kappos
*Director of the United States Patent and Trademark Office*